US006461865B1

(12) United States Patent
Dedhar et al.

(10) Patent No.: US 6,461,865 B1
(45) Date of Patent: Oct. 8, 2002

(54) CALRETICULIN-DEFICIENT CELLS

(76) Inventors: Shoukat Dedhar, 255 East 19th Street, North Vancouver, British Columbia (CA), V7L 2Z1; Rene St-Arnaud, 1020 Clement Street, St. Laurent, Quebec (CA), H4L 1R9

( * ) Notice: Subject to any disclaimer, the term of this patent is extended or adjusted under 35 U.S.C. 154(b) by 0 days.

(21) Appl. No.: 09/065,894

(22) Filed: Apr. 23, 1998

Related U.S. Application Data

(60) Provisional application No. 60/043,963, filed on Apr. 23, 1997, and provisional application No. 60/080,331, filed on Apr. 1, 1998.

(51) Int. Cl.[7] .......................... C12N 15/85; C12N 15/86
(52) U.S. Cl. ................... 435/325; 424/93.2; 424/93.21; 424/93.7; 435/455; 435/463
(58) Field of Search .............................. 435/325, 975, 435/463, 455, 810, 93.21; 424/93.2, 93.7; 536/23.2

(56) References Cited

FOREIGN PATENT DOCUMENTS

WO          9623001          8/1996

OTHER PUBLICATIONS

Burns, K. et al., "Modulation of gene expression by calreticulin binding to the glucocorticoid receptor". Nature 367:476–480 (1994).
Capecchi, M.R. "The New Mouse Genetics: Altering the Genome by Gene Targeting", Trends Genet 5:70–76 (1989).
Coppolino, M.G. et al., "Calreticulin is essential for integrin–mediated calcium signalling and cell adhesion" Nature 386:843–847 (1997).
Coppolino, et al., "Calreticulin–knockout Embryonic Stem Cells are Deficient in Integrin–mediated Adhesion but not Calcium Stores" Mol. Cell Biol. 7, No. Supplement 1419 (1996).
Dedhar, S. et al., "Inhibition of nuclear hormone receptor activity by calreticulin" Nature 367 480–483 (1994).
D'Souza, R. et al., "Osteoblast–specific Expression of the α2(l) Collagen Promoter in Transgenic mice: Correlation with the Distribution of TGF–β1" J. of Bone and Mineral Research 8(9): 1127–1136 (1993).

Ecarot–Charrier, B. et al., "Osteoblasts isolated from Mouse Calvaria Initiate Matrix Mineralization in Culture", J. of Cell Biology 96:639–643 (1983).
Hogan B. et al., "Manipulating the Mouse Embryo" Section F, 254–290 Cold Spring Harbor Laboratory Press, N.Y. 1994.
Metzger, J.M., "Transition in Cardiac Contractile Sensitivity to Calcium during the In vitro Differentiation of Mouse Embryonic Stem Cells", J. Cell biol. 126(3):701–711 (1994).
Mortensen, R. M. et al., "Production of Homozygous Mutant ES Cells with a Single Targeting Construct" Mol. Cell Biol. 12(5):2391–2395 (1992).
Olson, Eric N. et al., "Molecular Pathways Controlling Heart Development" Science 272:671–676 (1996).
Robertson, E.J. "Embryo–derived stem cell lines" In Robertson E.J. ed. Teratocarcinoma and embryonic stem cells: a practical approach IRL Press, Oxford 71–112 (1987).
Rudnicki, M.A., et al., "Inactivation of MyoD in Mice Leads to up–regulation of the Myogenic HLH gene Myf–5 and Results in apparently normal Muscle Development" Cell 71:383–390 (1992).
Rudnicki M.A., et al., "Cell culture methods and induction of differentiation of embryonal carcinoma cell lines". In Robertson E.J. ed. Teratocarcinoma and embryonic stem cells: a practical approach IRL Press, Oxford 19–49 (1987).
Schmidt A., et al., "Transcriptional control of the Mouse α2(l) Collagen Gene: Functional Deletion Analysis of the Promoter and Evidence for Cell–specific Expression", Mol. Cell Biol. 6(2) 347–354 (1986).
St. Arnaud, R. et al., "Constitutive Expression of Calreticulin in Osteoblasts Inhibits Mineralization" J. Cell Biol. 131(5):1351–1359 (1995).
St. Arnaud, R. et al., "Vitamin D and Bone Development" in Feldman et al., Vitamin D, Academic Press Ch 18:293–303 (1997).
Sudo, H. et al., "In vitro Differentiation and Calcification in a New Clonal Osteogenic Cell Line Derived from Newborn a Mouse Calvaria" J. of Cell Biology 96:191–198 (1983).

Primary Examiner—David Saunders
Assistant Examiner—Amy DeCloux
(74) Attorney, Agent, or Firm—Burns, Doane, Swecker & Mathis, LLP

(57) ABSTRACT

The invention relates to calreticulin-deficient cells. The cells can be either homozygous or heterozygous for the calreticulin mutation.

3 Claims, 11 Drawing Sheets

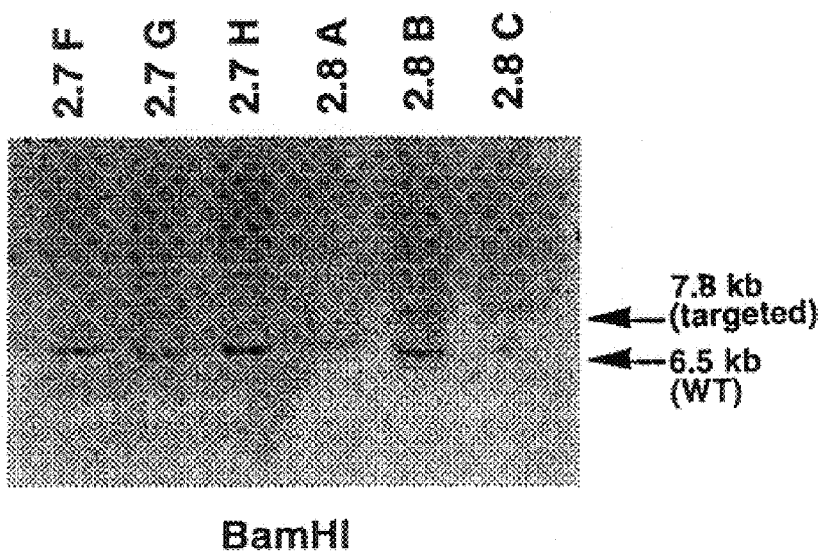
FIG. 1B
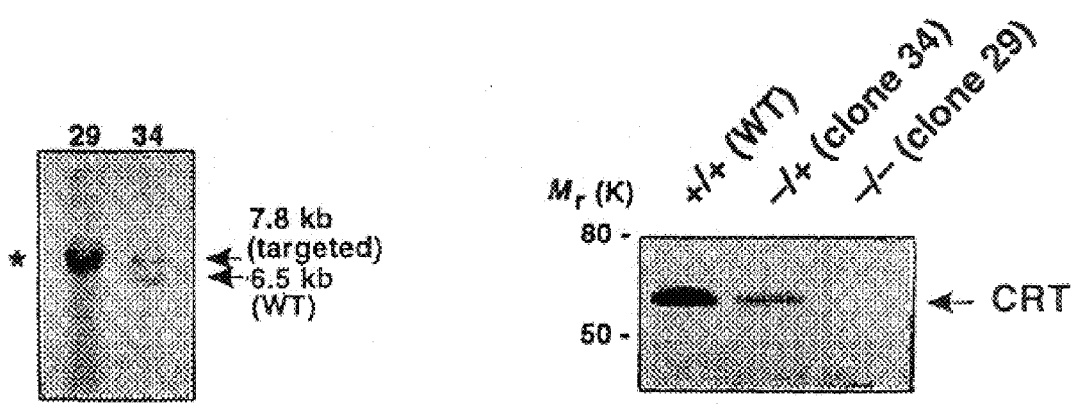
FIG. 1C
FIG. 1D

CALRETICULIN-DEFICIENT CELLS

CROSS-REFERENCE TO RELATED APPLICATIONS

This application claims the benefits of U.S. Provisional Application No. 60/043,963 filed on Apr. 23, 1997, and U.S. Provisional Application No. 60/080,331 filed on Apr. 1, 1998, both of which are incorporated by reference herein in their entirety.

BACKGROUND OF THE INVENTION

The physiology of many organs in mammals is regulated by hormones. These hormones include steroid hormones, thyroid hormones, metabolites of vitamins, such as all trans retinoic acid, 9-cis retinoic acid, vitamin D and its metabolite 1,25 dihydroxyvitamin D3. These hormones are proteins and bind to intracellular receptors which regulate expression of genes.

There are a variety of receptors which respond to hormones. Osteoblasts and osteoclasts respond to steroid hormones, vitamin D and retinoic acid. Mammary epithelial cells and breast carcinoma cells respond to estrogens, progesterone, retinoic acid and glucocorticoids. Lymphocytes respond to glucocorticoids.

The response of receptors to hormones is particularly important in the development of a number of diseases, including cancer, osteoporosis and chronic inflammatory disease. For example, the vitamin D receptor is strongly implicated in the evolution of osteoporosis.

The hormone receptor family is called the nuclear hormone receptor family and consists not only of receptors whose ligands are known, but also of an increasing number of orphan receptors whose ligands are unknown.

The nuclear hormone receptors can be divided into several domains which include the hormone (ligand) binding domain, the DNA-binding domain and the transactivation domain. The DNA-binding domain consists of two zinc fingers and is responsible for the receptor's binding to the DNA response elements which are found in the promoter and enhancer regions of the genes whose expression are regulated by these receptors. Once a hormone binds to its receptor, the receptor binds to the DNA thereby inducing gene transcription.

Proteins which modulate hormone receptor induced gene transcription are poorly understood. Such proteins are present in the nucleus of the cell and inhibit or promote the binding of a hormone to its receptor.

Calreticulin was initially identified as the major $Ca^{2+}$-storage protein in the sarcoplasmic reticulum of skeletal muscle. Subsequent work has revealed that the protein can also be detected in the endoplasmic reticulum of non-muscle tissues. Calreticulin has been considered to be a resident protein of the endoplasmic reticulum of a cell, where it is thought to behave as a calcium binding protein due to its high capacity calcium binding properties. Calreticulin possesses many diverse functional domains such as high affinity, low capacity- and low affinity, high capacity-$Ca^{2+}$-binding sites, a C-terminal KDEL endoplasmic reticulum retention signal, and a nuclear localization signal.

Calreticulin is also present in the nucleus of a cell, and it has been shown to have a consensus nuclear localization sequence which is highly homologous to that of histone proteins. Calreticulin is involved in DNA binding by nuclear hormone receptor and nuclear hormone receptor mediated gene transcription.

Calreticulin also plays a role in regulation of integrin activity. Calreticulin associates with the cytoplasmic domains of integrin subunits. Integrins are mediators of cell adhesion to extracellular ligands. They can transduce biochemical signals into and out of cells. The cytoplasmic domains of integrins interact with several structural and signalling proteins and participate in the regulation of cell shape, motility, growth and differentiation. The interaction between calreticulin and the cytoplasmic domains of integrin subunits can influence integrin-mediated cell adhesion to extracellular matrix.

To help design pharmaceuticals and therapies for certain diseases, one must understand the function of certain intracellular proteins, such as calreticulin, and their role in modulating hormone responsiveness. One must also understand the role of proteins, such as calreticulin, in integrin mediation of biochemical signals, extracellular calcium influx, cell adhesion and cell migration. Cells deficient in a protein can be used to study the physiological effects of the deficiency and identify substances to treat the deficiency. Substances may be also identified which activate or inhibit production of the protein or which affect the protein's activity in cells not deficient in the protein. These substances can be used to inhibit or activate DNA binding by nuclear hormone receptor or nuclear hormone receptor induced gene transcription. They could inhibit or activate integrin mediation of biochemical signals, extracellular calcium influx, extracellular calcium influx, cell adhesion or cell migration. Pharmaceuticals including such peptides or their mimetics could be used to inhibit or activate DNA binding by nuclear hormone receptor or nuclear hormone receptor induced gene transcription. They could inhibit or activate integrin mediation of biochemical signals, extracellular calcium influx, cell adhesion or cell migration. Gene therapy could be used to inhibit or activate DNA binding by nuclear hormone receptor or nuclear hormone receptor induced gene transcription. It could also be used to inhibit or activate integrin mediation of biochemical signals, extracellular calcium influx, cell adhesion or cell migration.

A need exists to identify calreticulin-deficient cells which can be used as a research tool to identify and evaluate the physiological effects of calreticulin. These cells could be used to identify substances which can treat calreticulin deficiency. These cells could also be used to identify substances which activate or inhibit calreticulin production and activity. This would lead to improved methods of treating a variety of diseases, disorders and abnormal physical states in mammals by regulating hormone receptor induced gene transcription in mammalian cells.

The advent of gene targeting technology, sometimes referred to as "gene knock-out", has allowed considerable insight into the role and function of particular gene products during development and differentiation. The technique relies on the use of pluripotent embryo-derived stem (ES) cells. An inactivating mutation is engineered into a cloned genomic fragment of the target gene and this mutated gene is introduced into ES cells cultured in vitro. Although the transfected mutant gene most frequently integrates randomly into the host cell's genome, powerful selection schemes have been designed that allow the identification and isolation of the rare cells that have incorporated the mutant gene at the corresponding targeted chromosomal location through homologous recombination, thus creating a null allele of the target gene. These cells are then micro-injected into the blastocoel cavity of a preimplantation mouse embryo and the blastocyst is re-implanted into the uterus of a foster mother. Strains of mice with different coat colors are normally selected for the ES cell population and the recipient blastocyst, thus allowing simple identification of the chimeric animals on the basis of fur color. Back-crossing breeding then allows one to determine if the ES cells have contributed to the germ line of the chimeric animals. The progeny that shows ES cells germ line transmission is genotyped to detect the animals that carry the engineered mutation. These heterozygote siblings are then interbred to obtain animals that are homozygous for the desired mutation.

We have successfully targeted the 25-hydroxyvitamin D 24-hydroxylase (24-OHase) gene (St-Arnaud et al. Targeted inactivation of the 24-hydroxylase gene in embryonic stem (ES) cells. Journal of Bone and Mineral Research 9 (Suppl 1): S290 (1994)). Targeted ES cells were injected into mouse blastocysts by an outside facility, the MRC Centre of Excellence for Transgenesis. One of the resulting chimeric mice has transmitted the targeted allele to its progeny; animals that are heterozygous for the engineered mutation are normal and fertile. Animals homozygous for the targeted 24-OHase mutation are born with the expected Mendelian frequency of 25% (36/154); however, about one-half of the homozygotes died within one week after birth. We suspect that the incomplete penetrance of the homozygous phenotype may be due to the mixed genetic background (129Sv× C57 Bl 6) of the animals and are currently back-crossing the mutation into the inbred 129Sv background. Preliminary data suggest a mild hypercalcemia in homozygous mutants; histological examination revealed normal bone structure. Homozygous animals that survive are fertile. Interestingly, preliminary results suggest that bone development was abnormal in homozygotes born of homozygous females. These analyses should yield valuable insight into the biological role of $24,25(OH)_2D_3$ in mineral homeostasis and bone development.

Calreticulin has been shown to regulate multiple functions in various cell types: calcium binding; cell attachment via its interaction with integrin receptors; and modulation of DNA binding by nuclear hormone receptor. Some of these roles of calreticulin may depend on strict stochiometric relationships between calreticulin and its target proteins. Inactivating one calreticulin allele alters this stoichiometry through a gene dosage effect and affect development of heterozygous mice. Since calreticulin has been shown to modulate the action of the AR, RAR and VDR, we concentrate on the morphology and function of some of the target tissues of these hormones: adrenal glands, gonads, lungs, and bone. Moreover, as cell attachment via the integrin receptors is compromised in heterozygous animals, they exhibit a higher incidence of carcinogenesis.

Calreticulin-deficient cells would greatly increase the ability to study the effects of calreticulin. These cells would allow identification of substances which affect calreticulin activity and production. These cells could also be used to identify substances which reverse the effects of calreticulin deficiency. There are currently no calreticulin-deficient cells available to researchers. There is a need for calreticulin-deficient cells which are stable. Ideally, cells that are homozygous and cells that are heterozygous for the calreticulin mutation would be isolated.

BRIEF DESCRIPTION OF THE DRAWINGS

FIG. 1 Targeted inactivation of the calreticulin gene in embryonic stem (ES) cells.

FIG. 1B A representative Southern blot showing three targeted targeted ES cell clones, in which one calreticulin allele is disrupted. These heterozygous clones were inoculated into mouse blastocysts to generate calreticulin-null mice.

FIG. 1C Southern blot of 'double knock-out' ES cell clones. The asterisk points to the twice targeted calreticulin alleles.

FIG. 1D Western blot of wild-type, heterozygous (one allele targeted, #34) and homozygous (both alleles targeted, #29) ES cell clones. Coomassie blue staining of the membrane demonstrated equal protein loading in all lanes (not shown).

FIG. 2 Characterization of ES cell adhesion.

FIG. 3 Rescue of 'knock-out' ES cell adhesion by transfection with calreticulin.

FIG. 4 Assessment of calcium storage in endomembrane compartments and of integrin-mediated cytosolic $[Ca^{2+}]$ transients in ES cells.

SUMMARY OF THE INVENTION

Figure 1A:
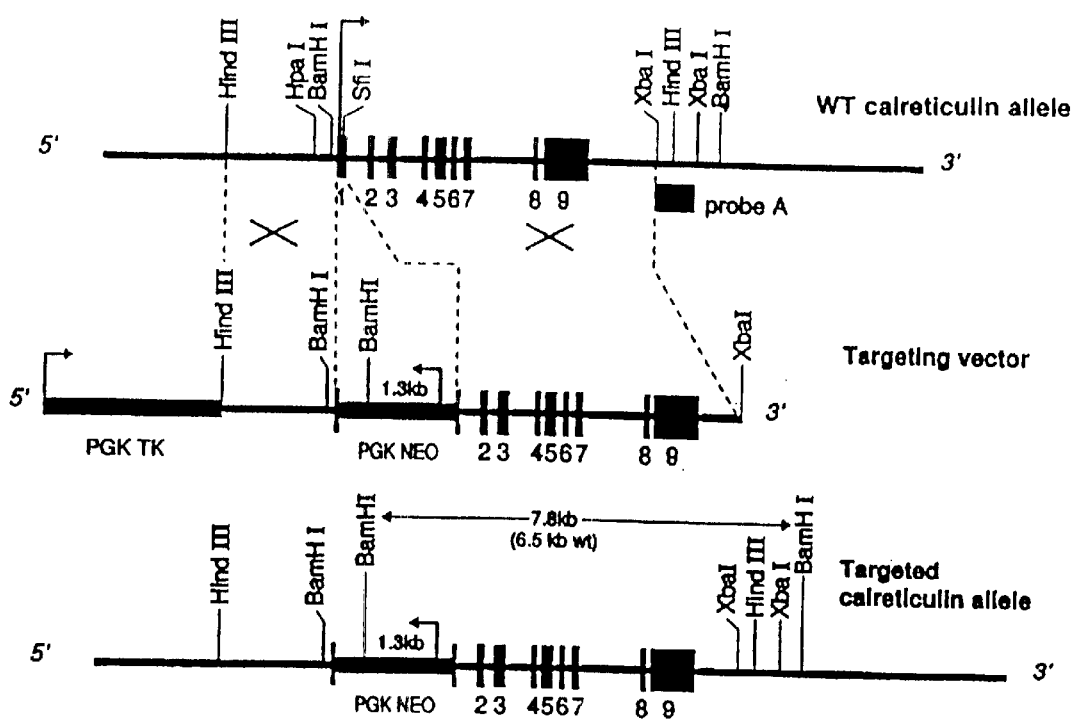
FIG. 1A The structure of the wild-type allele, targeting vector, and targeted allele are shown along with the pertinent restriction sites.

The invention consists of isolated calreticulin-deficient cells. The cells of this invention meet the need for calreticulin-deficient cells that can be used to study the effects of calreticulin. These cells allow identification of substances which affect calreticulin activity and production. These cells can also be used to identify substances which reverse the effects of calreticulin deficiency. The cells are stable. The invention includes cells that are homozygous and cells that are heterozygous for the calreticulin mutation.

The cells may be embryonic stem cells or embryonic fibroblasts. The cells may be isolated from a mammal. The cells are homozygous or heterozygous for a calreticulin gene mutation. In one embodiment of the invention, the calreticulin mutation can be engineered by inserting a cassette at the calreticulin gene start site. The cassette can be the PGKneo selection cassette.

Another embodiment of the invention is an assay for identifying a substance that affects integrin-mediated adhesion, integrin-initiated signaling, integrin-mediated cell migration, integrin-mediated influx of extracellular calcium, DNA binding by nuclear hormone receptor or nuclear hormone receptor mediated gene transcription using the isolated calcium-deficient cells. The invention also consists of a kit for identifying a substance that affects integrin-mediated adhesion, integrin-initiated signaling, integrin-mediated cell migration, integrin-mediated influx of extracellular calcium, DNA binding by nuclear hormone receptor or nuclear hormone receptor mediated gene transcription, which consists of the calcium-deficient cells.

The cells can be transformed or transfected with a heterologous gene. The cells can also be used to isolate genes, proteins or other compounds involved in calreticulin activity.

Another embodiment of the invention is a method for identifying a substance which affects integrin-mediated adhesion, integrin-initiated signaling, integrin-mediated cell migration, integrin-mediated influx of extracellular calcium, DNA binding by nuclear hormone receptor or nuclear hormone receptor mediated gene transcription which consists of introducing the substance to the calreticulin-deficient cells and determining whether the cells are affected by the presence of the substance.

We already isolated ES cell clones in which one allele of the calreticulin gene has been targeted. These clones are expanded and then injected into C57BL/6 embryos at the blastocyst stage using standard techniques. This last step is performed on a cost basis by the MRC Centre of Excellence for Transgenesis at the Montreal General Hospital, as previously mentioned (St. Arnaud et al.).

DETAILED DESCRIPTION OF THE INVENTION

Integrins are important mediators of cell adhesion to extracellular ligands and can transduce biochemical signals both into and out of cells[1,2]. The cytoplasmic domains of integrins interact with several structural and signaling proteins and consequently participate in the regulation of cell shape, motility, growth and differentiation[3]. It has previously been shown that calreticulin associates with the cytoplasmic domains of integrin subunits and that this interaction can influence integrin-mediated cell adhesion to extracellular matrix[4,5]. We have developed calreticulin-deficient embryonic stem (ES) cells and isolated embryonic fibroblasts from calreticulin mutant mice. In both cell types, integrin-mediated adhesion was severely impaired, though integrin expression was not altered. Expression of recombinant calreticulin in 'double knock-out' ES cells by cDNA transfection rescued integrin-mediated adhesion. In wild-type cells, engagement of surface integrins induced a transient elevation in cytosolic calcium concentration ($[Ca2+]i$) due to influx of extracellular calcium. This calcium transient was absent in calreticulin-deficient cells. In contrast, the, amount of calcium in endomembrane stores, both inositol 1,4,5-trisphosphate- and thapsigargin-sensitive, was indistinguishable in the two cell types. These results demonstrate that calreticulin is an essential modulator of both integrin adhesive functions and integrin-initiated signaling, but that it may not play a significant role in the storage of luminal calcium.

The cells are useful in identifying drugs for treatment of calreticulin deficiency and for cells that either enhance or inhibit calreticulin expression. Potential drugs or known drugs may be screened with the cells to determine the efficacy of the drugs. Different treatment protocols and dosages can also be tested with the cells. Screening for drugs is done according to techniques known in the art. For example, a potential drug may be administered to the cells in different dosages. The cells are then assayed for the effect of the drug on the cells using techniques known in the art.

EXAMPLE 1

Development of Calreticulin-deficient Embryonic Stem Cells

ES cells targeted at one calreticulin allele were engineered by inserting the PGKneo[6] selection cassette in the antisense orientation at the calreticulin start site through homologous recombination (FIG. 1a)[7]. Other selection cassettes or variants of the PGKneo cassette may also be used to target the calreticulin allele. ES cells homozygous for the calreticulin mutation (double knock-out) were isolated by culturing calreticulin-targeted ES cells in increased G418 concentrations. The heterozygous and homozygous genotypes were demonstrated by Southern blotting (FIGS. 1b and c, respectively) and the null calreticulin phenotype was confirmed by immunoblotting with calreticulin antibodies (FIG. 1d). Three clones of ES cells were used extensively for the studies described here; parental cells (WT), a heterozygous clone (#34) and a homozygous clone (#29).

EXAMPLE 2

Growth Rates of ES Cells

Figure 2A:
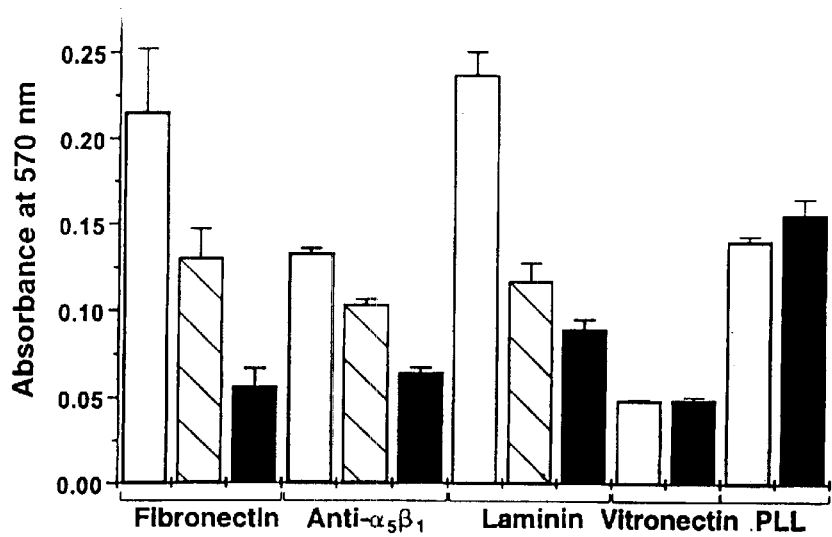
FIG. 2A Attachment of ES cell clones to fibronectin, anti-51 antibodies, laminin, vitronectin, and poly-L-lysine. Open bars, wild-type cells; hatched bars, clone #34 (−/+); solid bars, clone #29 (−/−). Inset: Photograph of cells on fibronectin.
Figure 2B:
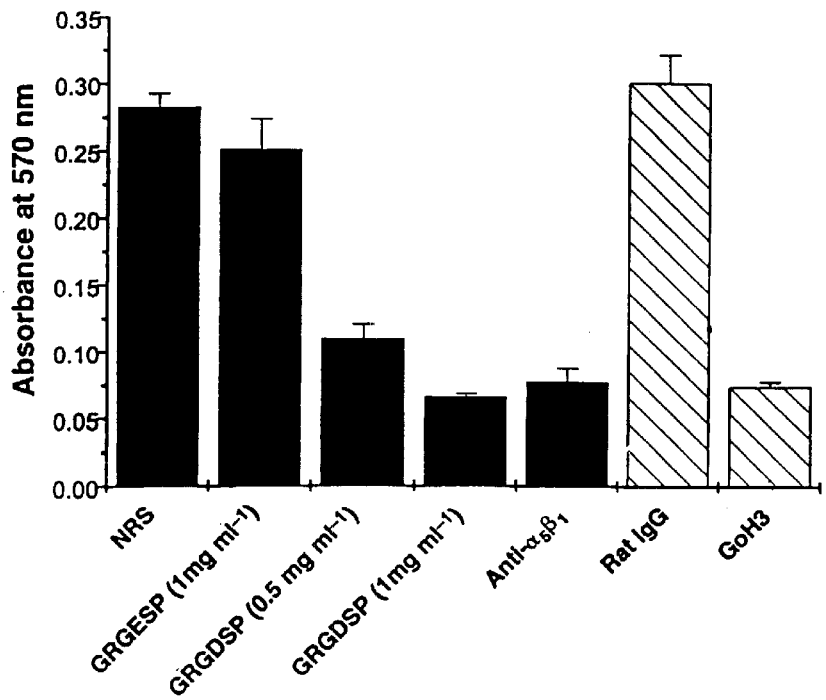
FIG. 2B Inhibition of wild-type ES cell attachment to fibronectin and laminin. Antisera were used at 10 $\mu$g/ml. NRS, normal rabbit serum. Solid bars, attachment to fibronectin; hatched bars, attachment to laminin. In A and B, means and SEM are cumulated from at least three independent experiments.
Figure 2C:
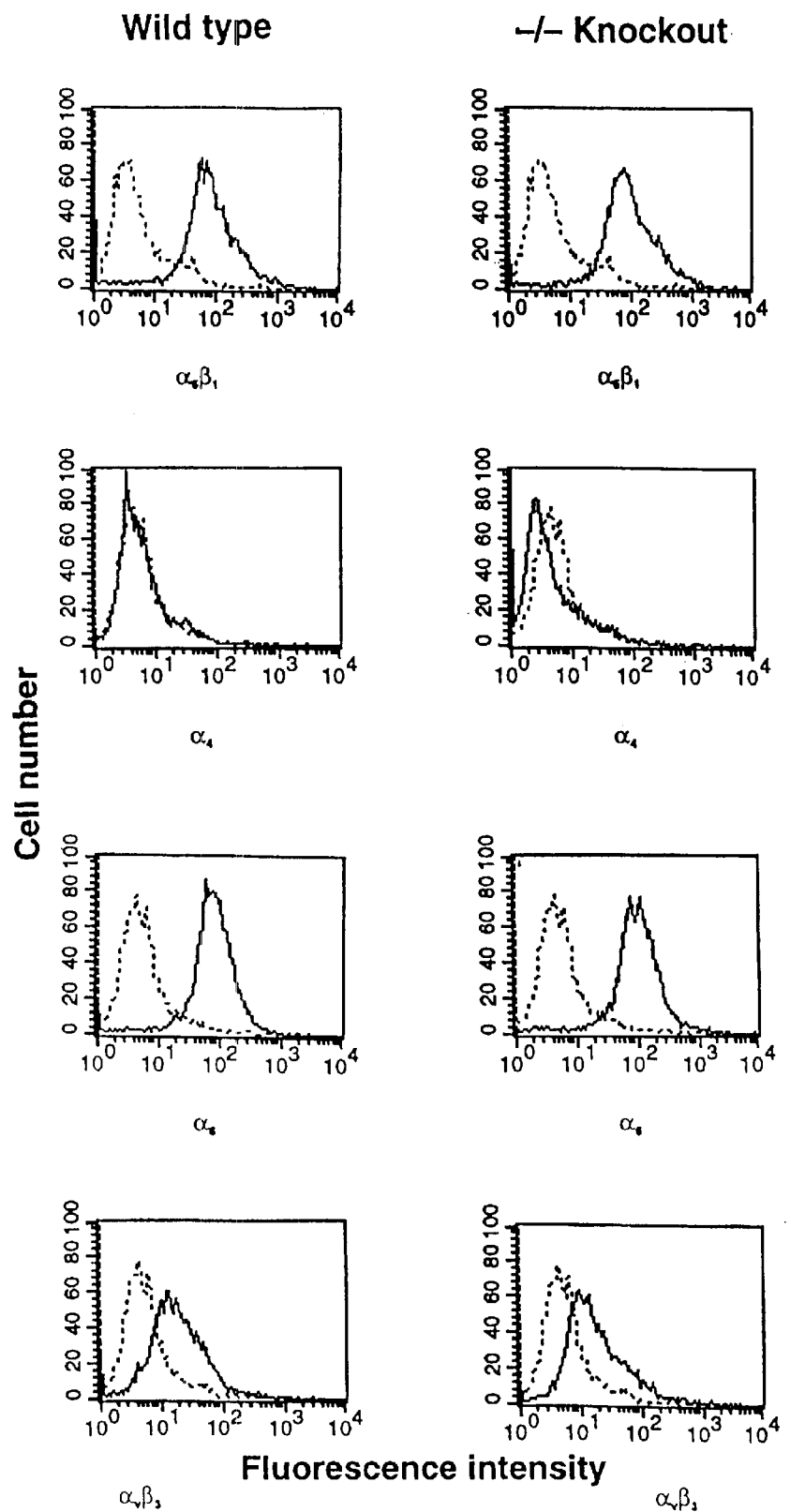
FIG. 2C Quantitation of cell surface integrin expression by flow cytometry of wild-type and clone #29 (−/−) ES cells.

The growth properties of the ES cell clones were assessed in media containing 10% serum and all clones were found to have similar growth rates (data not shown). The adhesive capacities of the ES cell clones were assessed by quantitative cell attachment assays on fibronectin and laminin under serum-free conditions. The WT cells adhered to fibronectin and laminin, whereas the adhesion of the cells lacking calreticulin (clone #29) was significantly reduced on these substrates (FIG. 2a). ES cells lacking calreticulin also were impaired in their ability to adhere to anti-alpha5 beta1 integrin antibodies (FIG. 2a). The heterozygous clone (#34) was generally intermediate in its level of adhesion. None of the clones tested adhered to vitronectin (FIG. 2a). Wild-type ES cell adhesion to ECM proteins was integrin-mediated since both GRGDSP peptides [SEQ ID No: 1] and a function-blocking polyclonal anti-fibronectin receptor serum inhibited adhesion to fibronectin, and cell attachment to laminin was inhibited by a monoclonal antibody (GoH3) to the integrin 6 subunit (FIG. 2b). To ensure that the observed differences in cell adhesion were not due to differences in the level of expression of the relevant integrins, the cell surface levels of $alpha_5$ $beta_1$, $alpha_4$, $alpha_6$ and $alpha_v$ $beta_3$ integrins were assessed by flow cytometry. All clones tested expressed similar levels of integrin subunits (FIG. 2c).

EXAMPLE 3

Isolated Fibroblasts Lacking Calreticulin

We were also able to isolate fibroblasts from mouse embryos lacking calreticulin. The knockout fibroblasts had markedly impaired integrin-mediated adhesion to fibronectin and vitronectin without alterations in levels of expression of $alpha_5$ $beta_1$ and $alpha_v$ $beta_3$.

EXAMPLE 4

Calreticulin Modulates Integrin Function in ES Cells

Figure 3A:
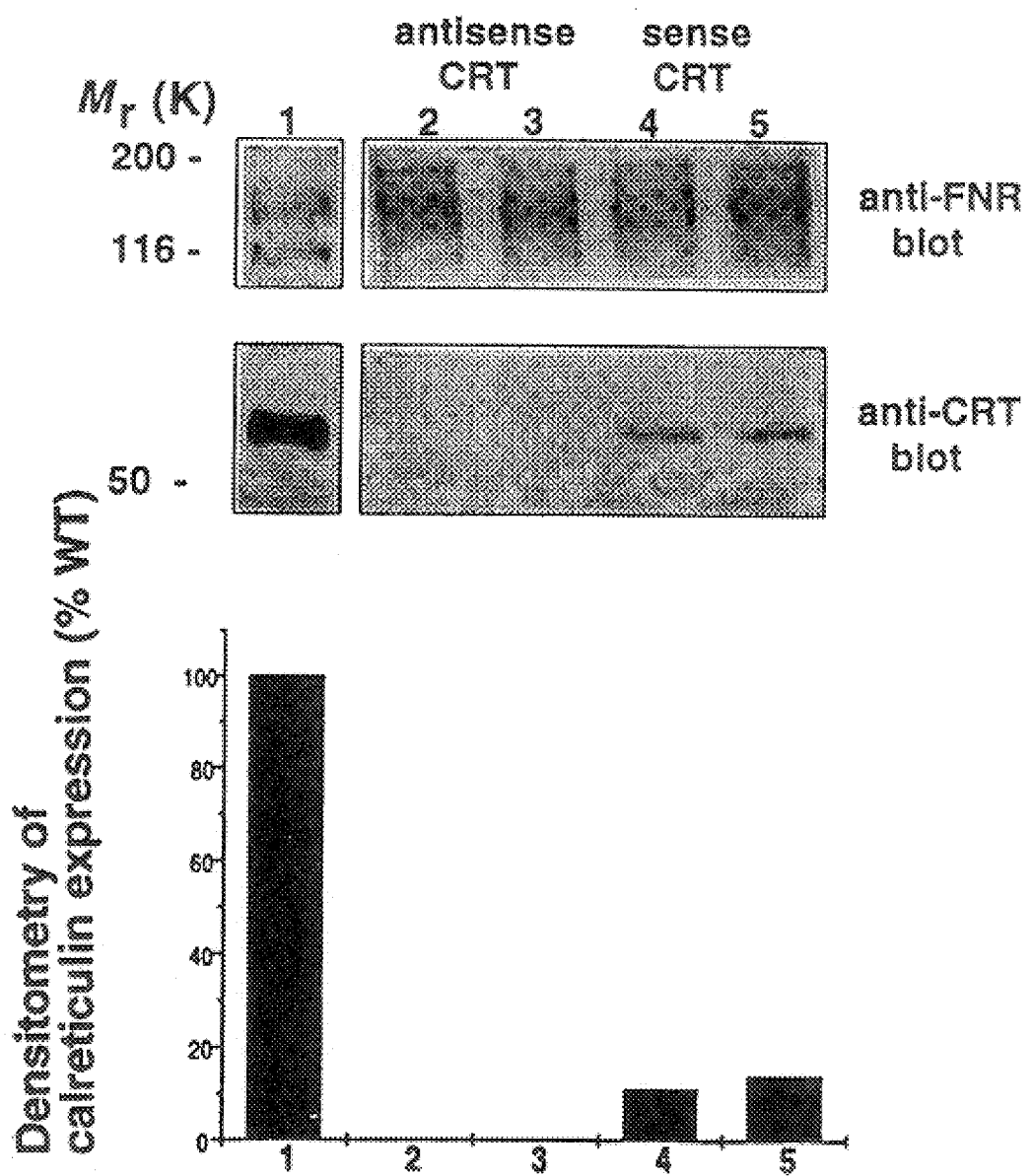
FIG. 3A Expression of calreticulin in ES cell clone #29 by transfection with pRC/CMV-calreticulin. Western blot of cell lysates from 4 independent transfections is shown with corresponding anti-fibronectin receptor blot. Lane 1, wild-type ES cell lysate; lanes 2 and 3, clone #29 cells transfected with antisense calreticulin; lanes 4 and 5, clone #29 cells transfected with sense calreticulin. In the bottom panel, densitometic quantitation of calreticulin expression, per $\mu$g of lysate, is shown.
Figure 3B:
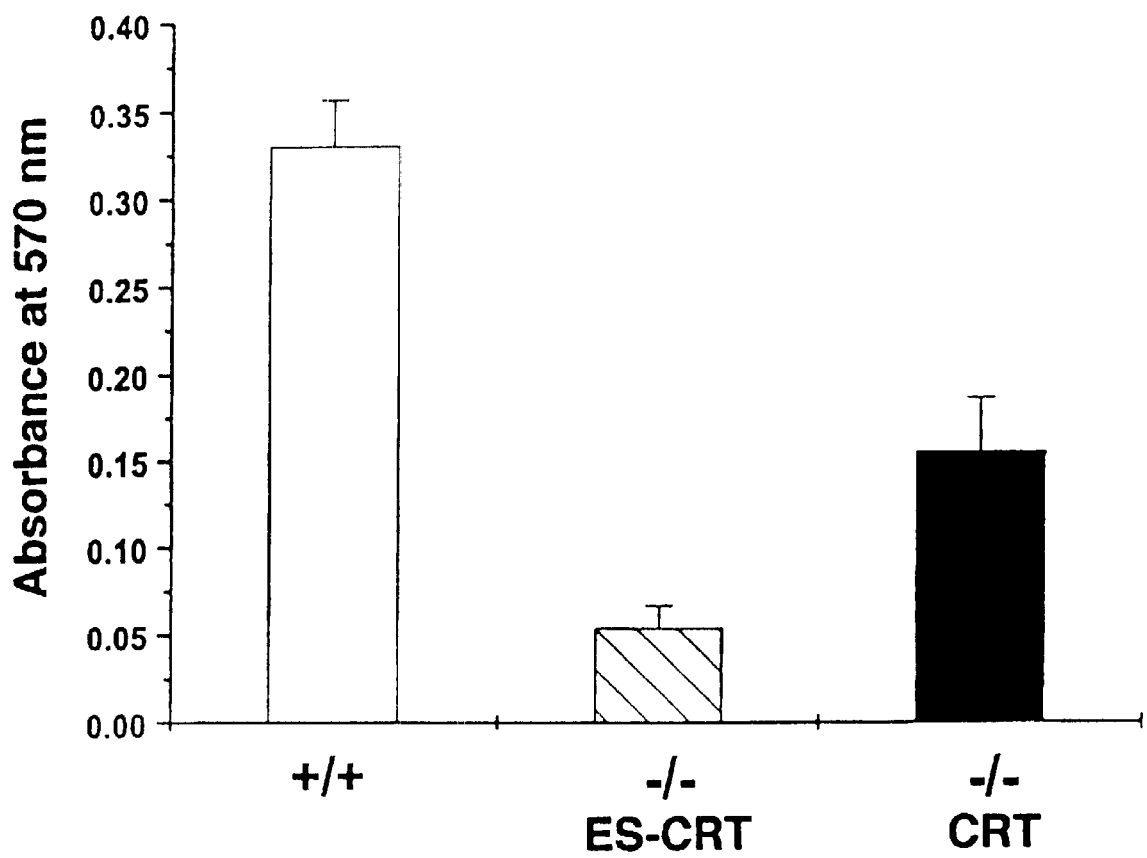
FIG. 3B Attachment of ES cell clone #29 transfectants to fibronectin. Open bar, wild-type ES cells; hatched bar, ES cell clone #29 transfected with antisense calreticulin (AS-CRT); solid bar, ES cell clone #29 transfected with sense calreticulin (CRT). Means and standard errors are cumulated from 5 independent experiments. The attachment of CRT transfectants is significantly greater (p<0.05) than that of AS-CRT transfectants.

To show the role of calreticulin in modulating integrin function in ES cells, we introduced calreticulin into calreticulin-negative ES cells (clone 29) by transient transfection with the pRC/CMV expression vector containing a 1.8 kb full length calreticulin cDNA. As a control, transfections were also carried out with pRC/CMV containing calreticulin cDNA in the antisense orientation. Calreticulin expression in clone 29 transfectants was confirmed by immunoblotting (FIG. 3a). These cells demonstrated significantly increased adhesion to fibronectin, compared to the antisense transfected cells in which there was no calreticulin expressed (FIG. 3b).

EXAMPLE 5

Calcium Regulation in the Wild-type and Calreticulin Knockout ES Cells

Figure 4A:
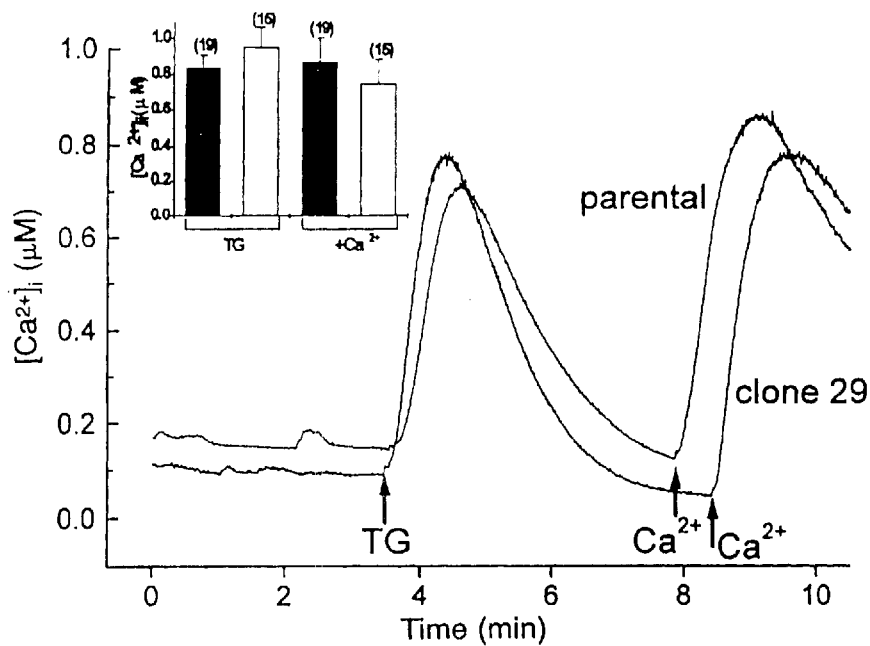
FIG. 4A Cytosolic $[Ca^{2+}]$ in adherent ES cells. Where indicated, thapsigargin (TG, 100 nM) and, subsequently, 1 mM free calcium were added to the medium. Representative traces are shown. Inset: Average peak $[Ca2+]i$ attained in parental (stippled bar; =19) or knock-out (clone 29, open bar; n=15).

Since calreticulin has been implicated in regulating calcium signaling, especially in the endoplasmic reticulum[8-10], we examined calcium regulation in the wild type and calreticulin 'knock-out' ES cells. The resting [Ca2+]i levels of parental and calreticulin-deficient cells were similar. More importantly, the cytosolic [$Ca^{2+}$] transient elicited by addition of thapsigargin to cells bathed in $Ca^{2+}$-free medium (FIG. 4a), which is a measure of the calcium stored in the endoplasmic reticulum, was also indistinguishable in the two cell types (FIG. 4a). Subsequent addition of extracellular calcium resulted in a large and sustained increase in cytosolic [$Ca^{2+}$] (FIG. 4a). This increase, which is attributable to opening of plasmalemmal channels in response to the depletion of endomembrane stores, was of comparable magnitude in wild-type and calreticulin-deficient cells (FIG. 4a). Because the cytosolic calcium buffering power of the two cell types (determined by loading the cytosol with varying doses of an exogenous calcium chelator[11]) was similar (FIG. 4c), these findings imply that calreticulin is not required to signal capacitative calcium influx across the plasma membrane and that it is not critical for luminal calcium storage in the endoplasmic reticulum of ES cells.

EXAMPLE 6

Figure 4B:
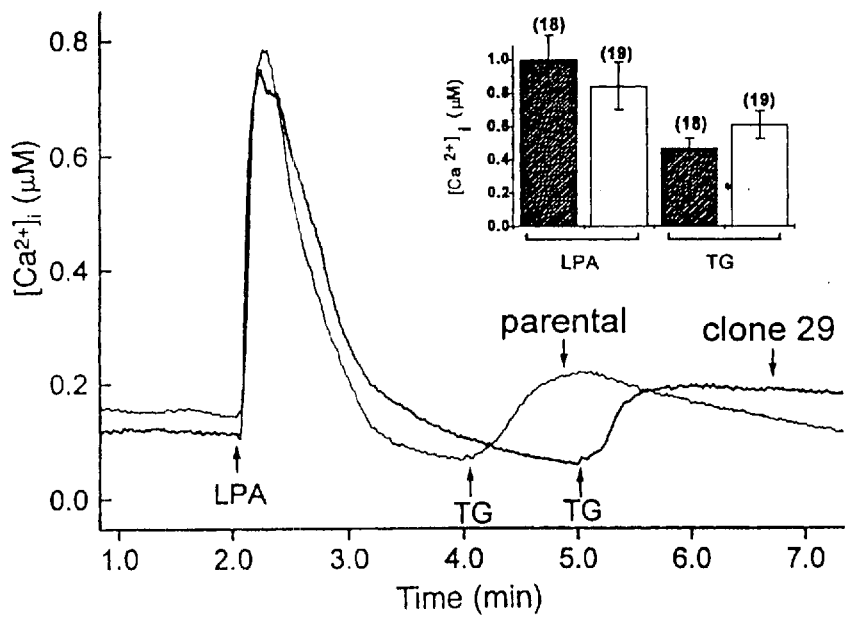
FIG. 4B As in A, except where indicated cells were stimulated with lysophosphatidic acid (LPA, 100 nM) followed by thapsigargin. Inset: Average peaks of $[Ca2+]_i$ attained in parental (stippled bar; n=18) and knock-out cells (clone 29, open bar; n=19).
Figure 4C:
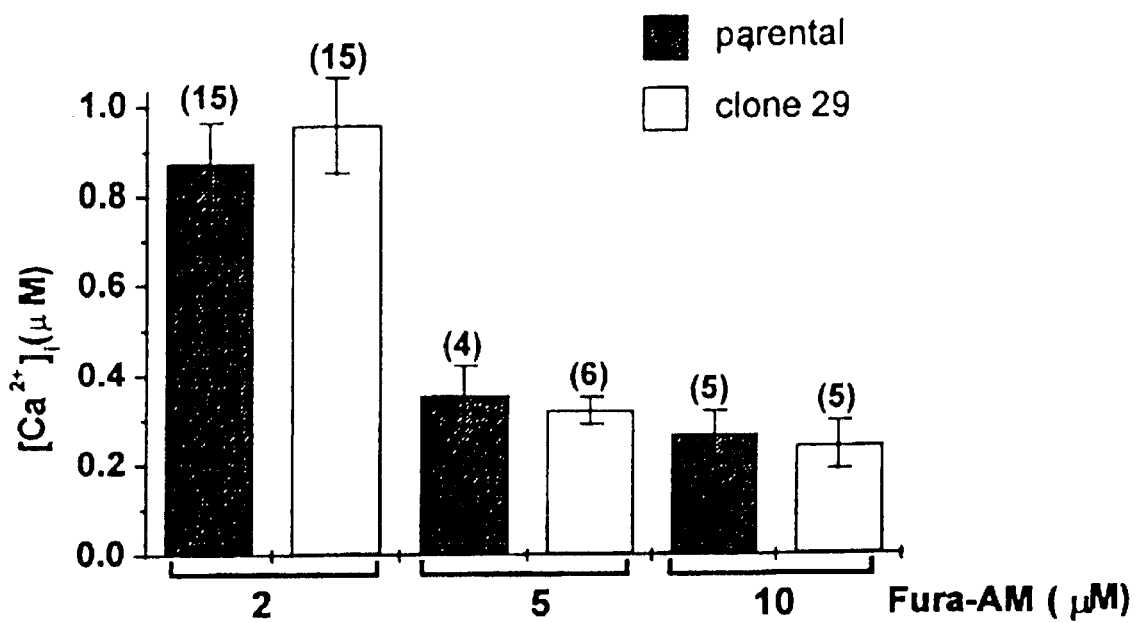
FIG. 4C Comparison of the cytosolic calcium buffering power in parental and knock-out ES cells. The peak $[Ca2+]_i$ induced by thapsigargin was measured in cells incubated with the indicated concentrations of the acetoxymethyl ester precursor of fura-2. The number of experiments is indicated in parentheses.

Role of Calreticulin in the Storage and Mobilization of Calcium from $InsP_3$-Sensitive Stores It has been reported that calreticulin can regulate inositol 1,4,5-trisphosphate ($InsP_3$)-mediated calcium signaling in Xenopus oocytes[9]. To more specifically examine the role of calreticulin in the storage and mobilization of calcium from $InsP_3$-sensitive stores, we challenged ES cells with lysophosphatidic acid (LPA, 100 nM), which induces $InsP_3$ release12 via heterotrimeric G-protein -mediated activation of phospholipase C. As shown in FIG. 4b, when added to cells in $Ca^{2+}$-free medium, LPA induced a rapid [Ca2+]i transient. The magnitude of this transient was indistinguishable in parental and clone 29 cells (FIG. 4b). Subsequent addition of thapsigargin induced a second, smaller burst of net $Ca^{2+}$ release that was considerably smaller than that reported in FIG. 4a. These observations imply that the stores depleted by LPA represent a subset of the thapsigargin-sensitive compartment. The amount of $Ca^{2+}$ released by thapsigargin after LPA was also not significantly different in parental and calreticulin-null cells (FIG. 4b). These findings suggest that calreticulin is not required for the initial $InsP_3$-sensitive Ca2+ release and although the decay phase of Ca2+ release in clone 29 cells seems slower than in ES cells (FIG. 4b), this was not found to be consistent in all cells examined. Our findings are in contrast to a previous report in which the $Ca^{2+}$ response to bradykinin was diminished as a result of antisense oligonucleotide down regulation of calreticulin expression[13], however our data clearly demonstrate that $Ca^{2+}$ storage in the ER and $InsP_3$-mediated $Ca^{2+}$ release are unaffected in the absence of calreticulin. While our findings are in partial agreement with those of Bastianutto et al.[14], who found that the level of calreticulin had no effect on the initial peak of $InsP_3$-sensitive $Ca^{2+}$ release, these investigators did find that subsequent oscillations of $Ca^{2+}$ could be affected by overexpression of calreticulin. Our results are also generally consistent with those of Camacho and Lechleiter[9] who found that $InsP_3$-mediated $Ca^{2+}$ release could be regulated by calreticulin, but that this function of calreticulin does not correlate with its capacity to store $Ca^{2+}$ and therefore suggests a 'signaling' function for calreticulin in $Ca^{2+}$ metabolism beyond mere sequesteration.

Figure 4D:
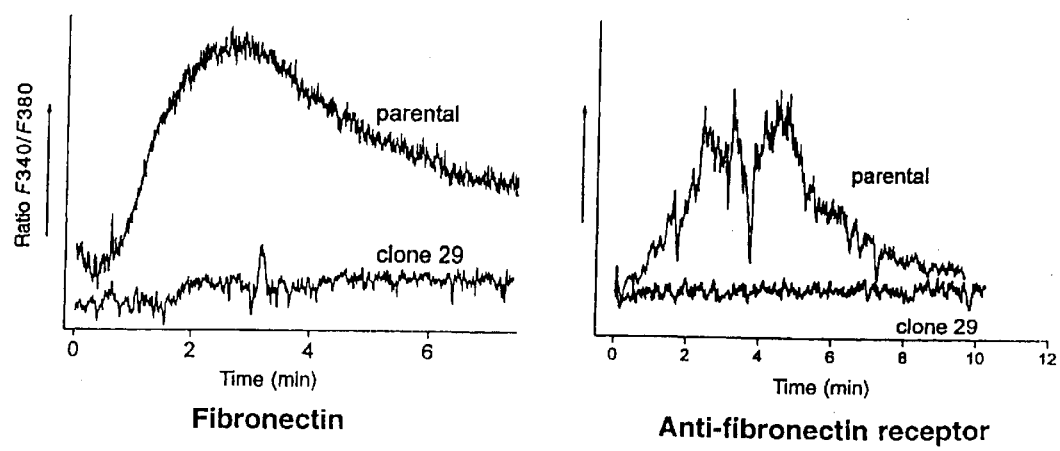
FIG. 4D Transient increases in $[Ca2+]_i$ in ES cells plated on fibronectin (representative of 9 wild-type and 9 knock-out cells) or anti-fibronectin receptor antiserum (representative of 16 wild-type and 9 knock-out cells).

One of the earliest responses reported to accompany integrin-mediated cell spreading is a stimulation of $Ca^{2+}$ influx[15,16]. Because ES cells lacking calreticulin failed to undergo normal adhesion and spreading on ECM substrates, we examined integrin-mediated calcium signaling by monitoring the fluorescence of fura-2-loaded cells as they interacted with glass coverslips coated either with an anti-$alpha_5$ $beta_1$ integrin antibody or with fibronectin (FIG. 4d). In the majority of the wild-type cells studied, engagement of surface integrins induced an elevation of cytosolic [$Ca^{2+}$] (e.g. FIG. 4d) that was often accompanied by visible spreading of the cells on the substratum. This elevation was due primarily to influx of extracellular $Ca^{2+}$, as it was eliminated when the cells attached in $Ca^{2+}$-free medium (n=12, data not shown). By contrast, the vast majority of calreticulin-null cells failed to spread and showed no detectable changes in cytosolic [$Ca^{2+}$] (FIG. 4d).

Figure 4E:
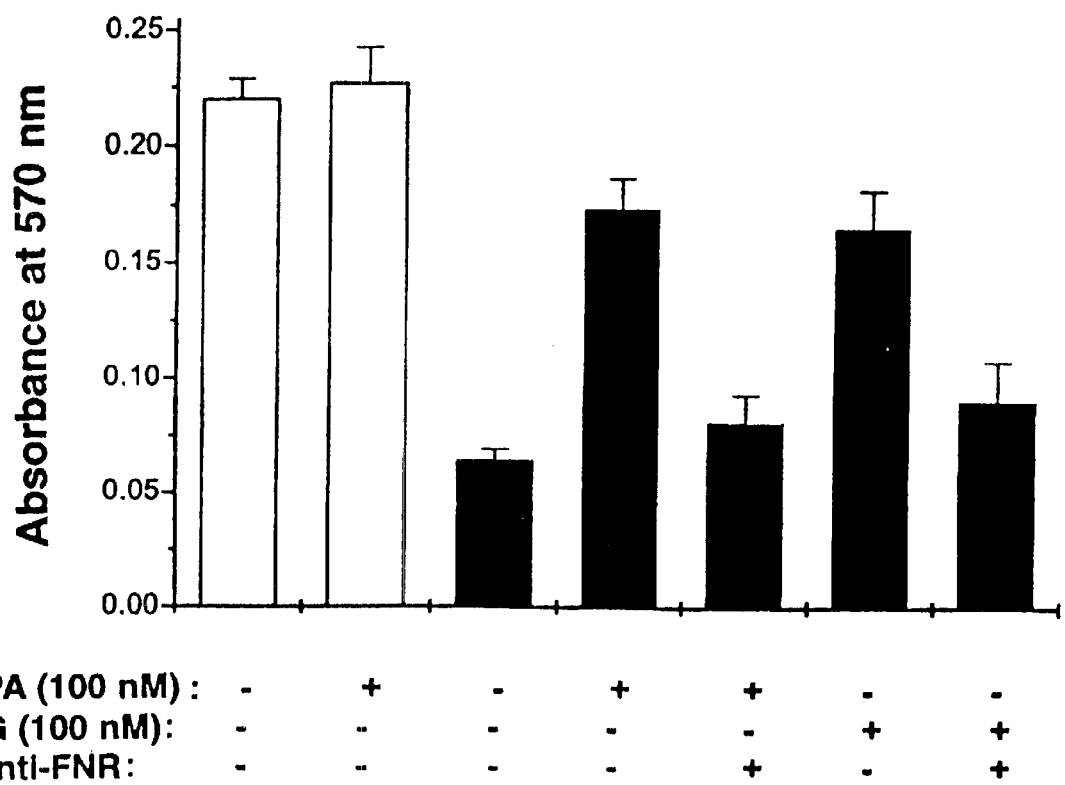
FIG. 4E Adhesion assays to Fibronectin as in FIG. 6. Where indicated 100 nM LPA or 100 nM Tg and anti-FNR antiserum (10 µg/ml) were added. Open bars, parental ES cells; closed bars, knock-out ES cells. All data are means +/− SEM of at least 3 experiments.

It is conceivable that a transient increase in cytosolic [$Ca^{2+}$] shortly after integrin ligand binding is an important part of normal receptor post-occupancy events (eg. increases in avidity, cytoskeletal reorganization). To examine this possibility, we tested whether stimulation of down-stream events in integrin 'outside-in' signaling within calreticulin-null cells could compensate for their adhesion defect. We found that when calreticulin knock-out cells were treated with 100 nM LPA their adhesion to fibronectin was significantly restored (FIG. 4e). Although not shown in FIG. 4, the response to LPA was dose-dependent. Similar results were obtained when the calreticulin −/− cells were treated with thapsigargin (FIG. 4e). Together these results suggest that stimulation of intracellular signaling events down-stream of integrin occupancy, possibly through a transient increase in cytosolic [$Ca^{2+}$] alone, can compensate for the loss of calreticulin-dependent adhesion.

EXAMPLE 7

Impaired Differentiation of Embryonic Stem Cells Deficient for Calreticulin

Embryonic stem (ES) cells can be induced to differentiate along several lineages in vitro, including hemopoietic, neuroectodermal, and cardiomyocytic (30). To determine the involvement of the multifunctional protein, calreticulin, in the proper differentiation of cardiac muscle cells, we have used the line of ES cells deficient for both alleles of the calreticulin gene (31).

Heterozygote and mutant homozygote cells were induced to differentiate into cardiac myocytes by culturing them as embryoid bodies in hanging drop cultures (32) in the presence of 1% dimethyl sulfoxide (DMSO) (33). Following five days in hanging drop cultures, the embryoid bodies were plated back individually on culture-grade multi-well plates, without DMSO, and scored for the presence of contracting cardiac myocytes five days later (day 10 from the beginning of the culture).

Figure 5:
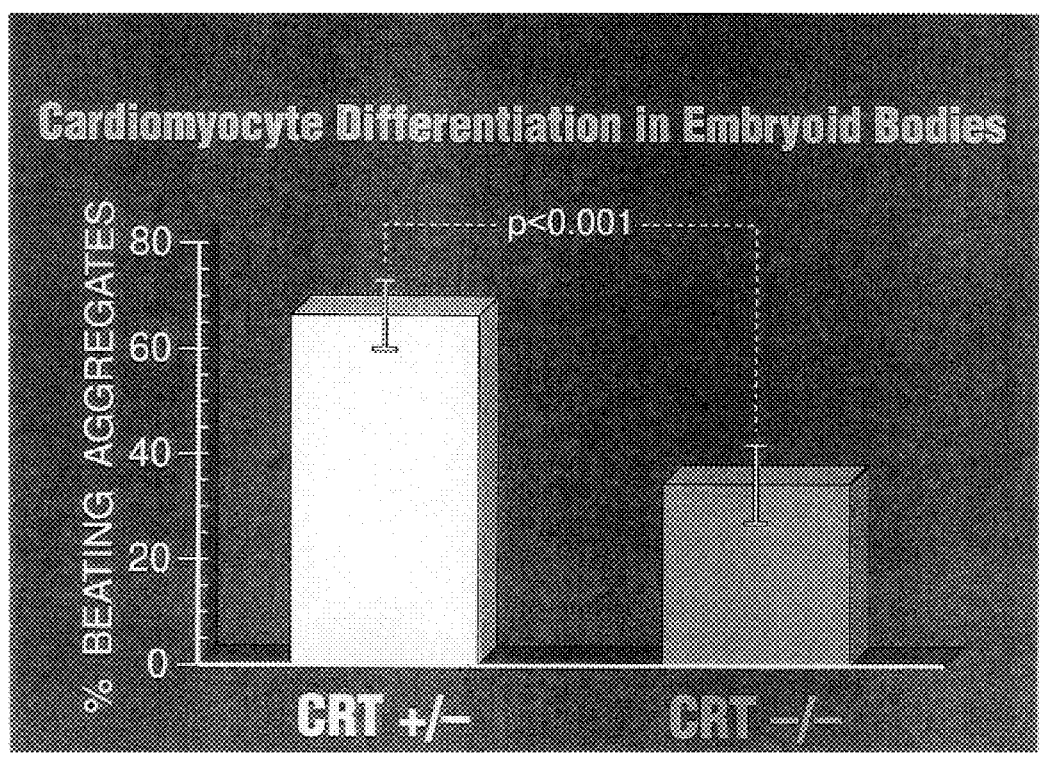
FIG. 5 Results of two independent experiments in which 48 embryoid bodies of each genotype were scored.

FIG. 5 shows the results of two independent experiments in which 48 embryoid bodies of each genotype were scored. ES cells deficient for calreticulin (−/− genotype) were significantly impaired in their capacity to differentiate into beating foci of cardiac myocytes (34±5% vs. 67±6%—mean±SEM of −/− and +/−, respectively). These results are in agreement with the observed phenotypes of calreticulin-deficient mice which include abnormal heart development with markedly reduced numbers of cardiac myocytes (data not shown).

The calreticulin-deficient ES cells are thus a useful experimental system in studies aimed at understanding the molecular determinants of heart development.

Cardiomyocytes are terminally differentiated cells and thus cannot be regenerated when the loss of heart muscle by myocardial cell death results in cardiac failure. An understanding of the molecular events associated with cardiac cell differentiation will be critical to future efforts to regenerate human myocardium by gene therapy or pharmacologic intervention. Drugs aimed at modulating cardiac myocyte survival are tested in the system of calreticulin deficient cells. Because these cells are already impaired in their capacity to differentiate into cardiac muscle cells, they provide an experimental model for testing the efficiency of drugs that can increase the differentiation, growth, or survival of cardiomyocytes. Additionally, vectors for gene therapy could be tested for their effects on improving the differentiation of calreticulin-deficient embryonic stem cells into myocardial cells.

EXAMPLE 8

Impaired Migration of Neuroectodermal Cells Derived from Calreticulin-deficient Stem Cells We have shown that calreticulin-deficient embryonic stem cells exhibit deficient signaling through integrin receptors. Amongst other functions, integrins are involved in cell migration. We have therefore tested the capacity of differentiated cells derived from the calreticulin-deficient stems cells to migrate on tissue-culture grade plastic substratum.

The stem cells were differentiated along neuroectodermal lineages by cultivating them in hanging drop cultures in the absence of inducer for 4 days, followed by treatment of hanging drops with 0.5 $\mu$M retinoic acid for an additional period of 4 days. The embryoid bodies were then dissociated with a mild trypsin treatment and plated on tissue-culture grade dishes. Confluent cultures (comprising neuronal and glial cells) were scarred with a pipette tip and migration of the cells across the scar was monitored by microscopy. The cells derived from the calreticulin-deficient stem cells were consistently impaired in their capacity to migrate across the gap of the scar. The capacity of the cells to migrate on defined substratum (fibronectin, collagen, laminin, etc.) is assayed. Migration is affected in a substratum-dependent fashion.

The results support our previous findings of impaired integrin receptor function in the absence of calreticulin protein.

Calreticulin is an intensively studied protein that has been assigned calcium regulating functions in the endoplasmic reticulum[8-9] and has also been shown to associate with proteins in the cytoplasm, nucleus and extracellular compartments[17-20]. Here, we now provide some new insights into the cellular functions of calreticulin. We conclude the following: 1) calreticulin is essential for normal, integrin-mediated adhesion to extracellular matrix substrates, 2) the calcium storage functions of calreticulin are not essential, 3) lack of calreticulin perturbs integrin-mediated influx of extracellular $Ca^{2+}$, possibly contributing to the loss of integrin-mediated cell adhesion. In regard to this third conclusion, it is possible that in calreticulin-null cells integrin ligand binding per se is not impaired, but that decreased adhesion follows from the perturbation of early downstream signals such as $Ca^{2+}$ influx. Our finding that LPA can compensate for lack of calreticulin supports this notion. While it has been reported by others that calreticulin may influence cell adhesion through alteration in the level of expression of vinculin,[21] we have confirmed that there is no difference in the level of vinculin expression in wild-type or calreticulin −/− ES cells. Rather, we have now established that calreticulin has an essential role in the normal function of several integrin receptors, including early events in integrin-mediated outside-in signaling. The calreticulin-null cells will also be useful in the investigation of other postulated roles of calreticulin such as modulation of steroid hormone receptor function[22-24].

Materials and Methods

Targeting Vector

The full-length 1.9 kb human calreticulin cDNA[25] was used as a probe to isolate a 14 kb murine calreticulin genomic clone from a library constructed from DNA of the 129 Sv strain (Statagene Corp.). The PGKneo selection cassette[26] was inserted in the opposite orientation at the unique Sfi I site immediately downstream of the translation start site by blunt-end cloning. The PGKtk cassette[26] was then cloned at the 5'-Hind III site. The resulting targeting vector featured 2 kb of homologous sequence on the short arm and 5 kb of sequence homology on the long arm (FIG. 1a).

ES Cell Culture and Transfection

The R1 ES cell line was cultured and electroporated as described by Hogan et al.[27]. Colonies were picked after 8 days in selection medium and expanded as detailed elsewhere[27]. For isolating cells homozygous for the targeted allele, the heterozygous clone 2F (clone #34) was grown on feeder cells in 4 mg/ml G418[28]. Resistant colonies were picked after 9 days in high-concentration selection medium. To obtain expression of calreticulin in homozygous mutant ES cells, the pRC/CMV expression vector containing a 1.8 kb full length calreticulin cDNA in either the sense or the antisense orientation[23] was transiently transfected into ES cell clone #29 using lipofectin according to the manufacturer's instructions (Gibco/BRL).

Southern Blot Analysis

DNA was isolated from cultured cells as previously described[27] and tested for integration at the targeted locus by Southern blotting of Bam HI-digests. The probe used was a 1 kb Xba I genomic fragment located immediately downstream of the region of homology of the targeting vector.

Attachment Assays and Analysis of Integrin Expression

Serum-free adhesion assays are described elsewhere[5]. 0.5–1 mg/ml GRGDSP [SEQ ID No: 1] or GRGESP [SEQ. ID No: 2] peptide (Gibco/BRL), 10 µg/ml rabbit anti-fibronectin receptor (Gibco/BRL) or 10 µg/ml rat anti-alpha$_6$ (GoH3, AMAC, Inc.) was added where indicated. For flow cytometric analysis of integrin expression, $1\times10^6$ cells were incubated on ice for 30 min. with primary antibody; anti-FNR, anti-VNR (Gibco/BRL), anti-alpha$_6$ (GoH3) or anti-alpha$_4$29 in PBS/0.1% sodium azide/2.0% fetal bovine serum. Cells were washed and then incubated for 30 min. with secondary antibody; FITC-conjugated goat anti-rabbit or FITC-conjugated goat anti-rat (Jackson ImmunoResearch). Cells were fixed in PBS/1.0% paraformaldehyde, pelleted, resuspended in PBS and analyzed on a FACScan (Becton Dickinson Immunocytometry Systems).

Cytosolic Calcium Measurements

To measure cytosolic free calcium, the cells were loaded with fura-2 by incubation with 0.5–10 µM of the precursor acetoxymethyl ester for 20 min. at 37° C. Fura-2 ratio fluorescence measurements were performed on a Nikon Diaphot TMD microscope (Nikon Canada) equipped with a 100 W Xenon lamp, a shutter/rotating mirror/fiber optic assembly (RatioMaster, Photon Technologies), a Fluor 40x/1.3 oil-immersion objective and a high-sensitivity photometer (D-104, PTI) interfaced to a 386 computer (NEC) via a 12 bit A/D board (Labmaster, National Instruments). The cells were alternately excited at 340 nm and 380 nm while recording the emission at 510 nm. Photometric data were acquired at 10 Hz using the Oscar software (PTI). The microscope was equipped with a separate light source for long-wavelength transillumination (>620 nm), a 580 nm emission dichroic mirror and a separate video camera (MTI 72, Dage-MTI) to allow continuous Hoffmann-enhanced visualization of the cells during the fluorescence measurements. Cytosolic calcium buffering power was estimated by measuring the magnitude of calcium transients in cells loaded with increasing concentrations fura-2[11]. The intracellular concentration of fura-2 was measured at the isosbestic wavelength (360 nm) and compared to standards. Unless indicated otherwise, all measurements of cytosolic $[Ca^{2+}]$ were made in $Ca^{2+}$-free medium. To assess integrin-mediated $Ca^{2+}$ influx, coverslips were coated with polyclonal anti-alpha5 beta1 antiserum or with fibronectin (each at 10 µg/ml). In medium containing 1 mM $Ca^{2+}$, suspended ES cells were allowed to sediment onto the coverslips as [Ca2+]i and cell morphology were monitored continuously and simultaneously. The traces start at the time of contact of a single cell with the coated cover slip.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims. For example, the description demonstrates to one skilled in the art how to identify and isolate other types of calreticulin-null cells from different tissues.

All publications, patents and patent applications are herein incorporated by reference in their entirety to the same extent as if each individual publication, patent or patent application was specifically and individually indicated to be incorporated by reference in its entirety.

REFERENCES

The documents listed below are incorporated herein by reference to the extent that they supplement, explain, provide a background for, or teach methodology, techniques and/or compositions employed herein.

1. Hynes, R. O. Integrins: versatility, modulation, and signaling in cell adhesion. *Cell* 69, 11–25 (1992).
2. Schwartz, M. A., Schaller, M. D. and Ginsberg, M. H. Integrins: Emerging paradigms of signal transduction. *Annu. Rev. Cell Biol. and Dev. Biol.* 11, 549–600 (1995).
3. Dedhar, S. and Hannigan, G. E. Integrin cytoplasmic interactions and bidirectional transmembrane signaling. *Curr. Opin. Cell Biol.* 8, 657–669 (1996).
4. Coppolino, M. G. et al. Inducible interaction of integrin alpha$^2$ beta$^1$ with calreticulin: dependence on the activation state of the integrin. *J. Biol. Chem.* 270, 23132–23138 (1995).
5. Leung-Hagesteijn, C., et al. Cell attachment to extracellular matrix substrates is inhibited upon downregulation of expression of calreticulin, an intracellular integrin-subunit-binding protein. *J. Cell Sci.* 107, 589–600 (1994).
6. Mansour, S. L. Disruption of the proto-oncogene int-2 in mouse embryo-derived stem cells: a general strategy to targeting mutations to non-selectable genes. *Nature* 336, 348–352 (1988).
7. Capecchi, M. The new mouse genetics: altering the genome by gene targeting. *Trends Genet.* 5, 70–76 (1989).
8. Michalak, M. et al. Calreticulin *Biochem. J.* 285, 681–692 (1992).
9. Camacho, P. and Lechleiter, J. D. Calreticulin Inhibits Repetitive Intracellular $Ca^{2+}$ Waves. *Cell* 82, 765–771 (1995).
10. Mery, L. et al. Overexpression of calreticulin increases intracellular $Ca^{2+}$-storage and decreases store-operated $Ca^{2+}$ influx. *J. Biol. Chem.* 271, 9332–9339(1996).
11. von Tscharner, V., Deranleau, D. A. and Baggioloni, M. Calcium fluxes and calcium buffering in human neutrophils. *J. Biol. Chem.* 261, 10163–10168 (1986).
12. Jalink K., et al. Lysophosphatidic acid-induced $Ca^{2+}$ mobilization in human A431 cells: structure-activity analysis *Biochem J.* 307, 609–616 (1995)

13. Liu, N., et al. Decreasing Calreticulin Expression Lowers the $Ca^{2+}$ Response to Bradykinin and Increases Sensitivity to Ionomycin in NG-108-15 Cells. *J. Biol. Chem.* 269, 28635–28639 (1994).
14. Bastianutto, C. et al. Overexpression of Calreticulin Increases the $Ca^{2+}$ Capacity of Rapidly Exchanging $Ca^{2+}$ Stores and Reveals Aspects of Their Lumenal Microenvironment and Function. *J. Cell Biol.* 130, 847–855 (1995).
15. Schwartz, M. A. Spreading of Human Endothelial Cells on Fibronectin or Vitronectin Triggers Elevation of Intracellular Free Calcium. *J. Cell Biol.* 120, 1003–1010 (1993).
16. Sjaastad, M. D., Lewis, R. S. and Nelson, W. J. Mechanisms of integrin-mediated Calcium Signaling in MDCK Cells: Regulation of Adhesion by $IP_3$- and Store-independent Calcium Influx. *Mol. Biol. Cell* 1, 1025–1041 (1996).
17. Dedhar, S. Novel functions for calreticulin: interaction with integrins and modulation of gene expression? *Trends Biochem. Sci.* 19, 269–271 (1994).
18. Sontheimer, R. D. et al. The unveiling of calreticulin—a clinically relevant tour of modern cell biology. *J. Invest. Med.* 43, 362–370 (1995).
19. Rojiani, M. V. et al. In vitro interaction of a polypeptide homologous to human RO/SS-A antigen (calreticulin) with a highly conserved amino acid sequence in the cytoplasmic domain of integrin-subunits *Biochemistry* 30, 9859–9866 (1991).
20. Williams, M. J. et al. The inner world of cell adhesion: integrin cytoplasmic domains. *Trends Cell Biol.* 4, 109–112 (1994).
21. Opas, M. et al Calreticulin Modulates Cell Adhesiveness via Regulation of Vinculin Expression. *J. Cell Biol.* 135, 1913–1923 (1996).
22. Burns, K. et al. Modulation of gene expression by calreticulin binding to the glucocorticoid receptor. *Nature* 367, 476–480 (1994).
23. Dedhar, S. et al Inhibition of nuclear hormone receptor activity by calreticulin. *Nature* 367, 480–483 (1994).
24. St. Arnaud, R. et al. Constitutive expression of calreticulin in osteoblasts inhibits mineralization. *J. Cell Biol.* 131, 1351–1359 (1995).
25. McCauliffe, D. P. et al Molecular cloning, expression, and chromosome 19 localization of a human Ro/SS-A autoantigen. *J. Clin. Invest.* 86, 332–335 (1990).
26. Rudnicki, M. A. et al. Inactivation of MyoD in mice leads to up-regulation of the myogenic HLH gene myf-5 and results in apparently normal muscle development. *Cell* 71, 383–390 (1992).
27. Hogan, B. et al Manipulating the mouse embryo. (Cold Spring Harbour Laboratory Press, New York 1994).
28. Mortensen, R. M. Production of homozygous mutant ES cells with a single targeting construct *Mol. Cell. Biol.* 12, 2391–2395 (1992).
29. Miyake, K. et al Evidence for a role of the integrin VLA-4 in lympho-hemopoiesis *J. Exp.Med.* 173, 599–607 (1991).
30. Robertson, E. J. 1987. Embryo-derived stem cell lines. In: Robertson, E. J., ed., Teratocarcinomas and embryonic stem cells: a practical approach. IRL Press, Oxford, pp. 71–112.
31. Coppolino, M. R., M. J. Woodside, N. Demaurex, S. Grinstein, R. St-Arnaud, and S. Dedhar. 1997. Calreticulin is essential for integrin-mediated calcium signaling and cell adhesion. Nature 396:843–847.
32. Metzger J. M., W.-I. Lin, and L. C. Samuelson. 1994. Transition in cardiac contractile sensitivity to calcium during the in vitro differentiation of mouse embryonic stem cells. *J. Cell Biol.* 126: 701–711.
33. Rudnicki, M. A., and M. W. McBurney. 1987. Cell culture methods and induction of differentiation of embryonal carcinomal cell lines. In: Robertson, E. J., ed., Teratocarcinomas and embryonic stem cells: a practical approach. IRL Press, Oxford, pp. 19–49.

We claim:

1. Engineered calreticulin-deficient mammalian cells or progeny thereof, said cells being homozygous or heterozygous for a calreticulin gene mutation engineered by inserting an expression cassette at the calreticulin gene start site.

2. The engineered calreticulin deficient mammalian cells or progeny thereof of claim 1, wherein the expression cassette is the PGKneo selection cassette.

3. Engineered calreticulin deficient mammalian cells or progeny thereof, said cells comprising a calreticulin gene mutated by insertion of a PGKneo cassette proximate to the calreticulin gene start site so that the gene does not produce calreticulin.

* * * * *

SEQUENCE LISTING

```
<160> NUMBER OF SEQ ID NOS:  2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:peptide

<400> SEQUENCE: 1

Gly Arg Gly Asp Ser Pro
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:peptide

<400> SEQUENCE: 2

Gly Arg Gly Glu Ser Pro
 1               5
```